(12) United States Patent
Ameri et al.

(10) Patent No.: US 8,032,228 B2
(45) Date of Patent: Oct. 4, 2011

(54) METHOD AND APPARATUS FOR DISCONNECTING THE TIP ELECTRODE DURING MRI

(75) Inventors: Masoud Ameri, Maple Plain, MN (US); Greg P. Carpenter, Centerville, MN (US); David C. Olson, Eden Prairie, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 483 days.

(21) Appl. No.: 12/329,383

(22) Filed: Dec. 5, 2008

(65) Prior Publication Data

US 2009/0149906 A1    Jun. 11, 2009

Related U.S. Application Data

(60) Provisional application No. 60/992,991, filed on Dec. 6, 2007.

(51) Int. Cl.
*A61N 1/37* (2006.01)
(52) U.S. Cl. ............... 607/62; 607/9; 607/63; 600/411; 128/901
(58) Field of Classification Search .................. None
See application file for complete search history.

(56) References Cited

U.S. PATENT DOCUMENTS

| | | |
|---|---|---|
| 3,888,260 A | 6/1975 | Fischell |
| 3,898,995 A | 8/1975 | Dresbach |
| 4,091,818 A | 5/1978 | Brownlee et al. |
| 4,379,459 A | 4/1983 | Stein |
| 4,404,125 A | 9/1983 | Abolins et al. |
| 4,516,579 A | 5/1985 | Irnich |
| 4,611,127 A | 9/1986 | Ibrahim et al. |
| 4,694,837 A | 9/1987 | Blakeley et al. |
| 4,729,376 A | 3/1988 | DeCote, Jr. |
| 4,751,110 A | 6/1988 | Gulla et al. |
| 4,779,617 A | 10/1988 | Whigham |
| 4,869,970 A | 9/1989 | Gulla et al. |
| 4,934,366 A | 6/1990 | Truex et al. |
| 5,038,785 A | 8/1991 | Blakeley et al. |

(Continued)

FOREIGN PATENT DOCUMENTS

EP    0530006    3/1993

(Continued)

OTHER PUBLICATIONS

Dempsey Mary F. et al., "Investigation of the Factors Responsible for Burns During MRI", *Journal of Magnetic Resonance Imaging* 2001;13:627-631.

(Continued)

*Primary Examiner* — Kennedy Schaetzle
(74) *Attorney, Agent, or Firm* — Faegre & Benson LLP

(57) ABSTRACT

A medical device includes a pulse generator, a lead, and an electrode. The lead includes an electrode and a lead conductor connecting the pulse generator with the electrode via first and second conductive paths. The medical device includes first and second switches. The first switch includes a non-conductive state in the presence of a magnetic field, the non-conductive state preventing formation of the first conductive path between the pulse generator and the electrode. The second switch includes a non-conductive state that prevents formation of the second conductive path between the pulse generator and the electrode. The first switch in the non-conductive state and the second switch in the non-conductive state electrically shields the electrode from electromagnetic radiation and induced voltages during a magnetic resonance imaging procedure.

24 Claims, 8 Drawing Sheets

U.S. PATENT DOCUMENTS

| | | |
|---|---|---|
| 5,075,039 A | 12/1991 | Goldberg |
| 5,076,841 A | 12/1991 | Chen et al. |
| 5,120,578 A | 6/1992 | Chen et al. |
| 5,187,136 A | 2/1993 | Klobucar et al. |
| 5,188,117 A | 2/1993 | Steinhaus et al. |
| 5,197,468 A | 3/1993 | Proctor et al. |
| 5,217,010 A | 6/1993 | Tsitlik et al. |
| 5,243,911 A | 9/1993 | Dow et al. |
| 5,279,225 A | 1/1994 | Dow et al. |
| 5,288,313 A | 2/1994 | Portner |
| 5,292,342 A | 3/1994 | Nelson et al. |
| 5,309,096 A | 5/1994 | Hoegnelid |
| 5,325,728 A | 7/1994 | Zimmerman et al. |
| 5,345,362 A | 9/1994 | Winkler |
| 5,391,188 A | 2/1995 | Nelson et al. |
| 5,406,444 A | 4/1995 | Selfried et al. |
| 5,424,642 A | 6/1995 | Ekwall |
| 5,438,990 A | 8/1995 | Wahlstrand et al. |
| 5,454,837 A | 10/1995 | Lindegren et al. |
| 5,470,345 A | 11/1995 | Hassler et al. |
| 5,523,578 A | 6/1996 | Herskovic |
| 5,527,348 A | 6/1996 | Winkler et al. |
| 5,529,578 A | 6/1996 | Struble |
| 5,545,187 A | 8/1996 | Bergstrom et al. |
| 5,562,714 A | 10/1996 | Grevious |
| 5,607,458 A | 3/1997 | Causey, III et al. |
| 5,609,622 A | 3/1997 | Soukup et al. |
| 5,618,208 A | 4/1997 | Crouse et al. |
| 5,620,476 A | 4/1997 | Truex et al. |
| 5,647,379 A | 7/1997 | Meltzer |
| 5,649,965 A | 7/1997 | Pons et al. |
| 5,650,759 A | 7/1997 | Hittman et al. |
| 5,662,694 A | 9/1997 | Lidman et al. |
| 5,683,434 A | 11/1997 | Archer |
| 5,687,735 A | 11/1997 | Forbes et al. |
| 5,694,952 A | 12/1997 | Lidman et al. |
| 5,697,958 A | 12/1997 | Paul et al. |
| 5,709,225 A | 1/1998 | Budgifvars et al. |
| 5,714,536 A | 2/1998 | Ziolo et al. |
| 5,722,998 A | 3/1998 | Prutchi et al. |
| 5,727,552 A | 3/1998 | Ryan |
| 5,735,884 A | 4/1998 | Thompson et al. |
| 5,749,910 A | 5/1998 | Brumwell et al. |
| 5,751,539 A | 5/1998 | Stevenson et al. |
| 5,759,197 A | 6/1998 | Sawchuk et al. |
| 5,764,052 A | 6/1998 | Renger |
| 5,766,227 A | 6/1998 | Nappholz et al. |
| 5,776,168 A | 7/1998 | Gunderson |
| 5,782,891 A | 7/1998 | Hassler et al. |
| 5,792,201 A | 8/1998 | Causey, III et al. |
| 5,800,496 A | 9/1998 | Swoyer et al. |
| 5,800,497 A | 9/1998 | Bakels et al. |
| 5,814,090 A | 9/1998 | Latterell et al. |
| 5,817,130 A | 10/1998 | Cox et al. |
| 5,827,997 A | 10/1998 | Chung et al. |
| 5,853,375 A | 12/1998 | Orr |
| 5,867,361 A | 2/1999 | Wolf et al. |
| 5,869,078 A | 2/1999 | Baudino |
| 5,870,272 A | 2/1999 | Seifried et al. |
| 5,871,509 A | 2/1999 | Noren |
| 5,877,630 A | 3/1999 | Kraz |
| 5,895,980 A | 4/1999 | Thompson |
| 5,905,627 A | 5/1999 | Brendel et al. |
| 5,959,829 A | 9/1999 | Stevenson et al. |
| 5,964,705 A | 10/1999 | Truwit et al. |
| 5,968,854 A | 10/1999 | Akopian et al. |
| 5,973,906 A | 10/1999 | Stevenson et al. |
| 5,978,204 A | 11/1999 | Stevenson |
| 5,978,710 A | 11/1999 | Prutchi et al. |
| 5,999,398 A | 12/1999 | Makl et al. |
| 6,008,980 A | 12/1999 | Stevenson et al. |
| 6,031,710 A | 2/2000 | Wolf et al. |
| 6,032,063 A | 2/2000 | Hoar et al. |
| 6,055,455 A | 4/2000 | O'Phelan et al. |
| 6,079,681 A | 6/2000 | Stern et al. |
| 6,101,417 A | 8/2000 | Vogel et al. |
| 6,147,301 A | 11/2000 | Bhatia |
| 6,161,046 A | 12/2000 | Maniglia et al. |
| 6,162,180 A | 12/2000 | Miesel et al. |
| 6,173,203 B1 | 1/2001 | Barkley et al. |
| 6,188,926 B1 | 2/2001 | Vock |
| 6,192,279 B1 | 2/2001 | Barreras, Sr. et al. |
| 6,198,968 B1 | 3/2001 | Prutchi et al. |
| 6,198,972 B1 | 3/2001 | Hartlaub et al. |
| 6,209,764 B1 | 4/2001 | Hartlaub et al. |
| 6,217,800 B1 | 4/2001 | Hayward |
| 6,235,038 B1 | 5/2001 | Hunter et al. |
| 6,245,464 B1 | 6/2001 | Spillman et al. |
| 6,246,902 B1 | 6/2001 | Naylor et al. |
| 6,249,701 B1 | 6/2001 | Rajasekhar et al. |
| 6,268,725 B1 | 7/2001 | Vernon et al. |
| 6,270,831 B2 | 8/2001 | Kumar et al. |
| 6,275,369 B1 | 8/2001 | Stevenson et al. |
| 6,288,344 B1 | 9/2001 | Youker et al. |
| 6,324,431 B1 | 11/2001 | Zarinetchi et al. |
| 6,358,281 B1 | 3/2002 | Berrang et al. |
| 6,365,076 B1 | 4/2002 | Bhatia |
| 6,381,494 B1 | 4/2002 | Gilkerson et al. |
| 6,421,555 B1 | 7/2002 | Nappholz |
| 6,424,234 B1 | 7/2002 | Stevenson |
| 6,446,512 B2 | 9/2002 | Zimmerman et al. |
| 6,452,564 B1 | 9/2002 | Schoen et al. |
| 6,456,481 B1 | 9/2002 | Stevenson |
| 6,459,935 B1 | 10/2002 | Piersma |
| 6,470,212 B1 | 10/2002 | Weijand et al. |
| 6,487,452 B2 | 11/2002 | Legay |
| 6,490,148 B1 | 12/2002 | Allen et al. |
| 6,496,714 B1 | 12/2002 | Weiss et al. |
| 6,503,964 B2 | 1/2003 | Smith et al. |
| 6,506,972 B1 | 1/2003 | Wang |
| 6,510,345 B1 | 1/2003 | Van Bentem |
| 6,512,666 B1 | 1/2003 | Duva |
| 6,522,920 B2 | 2/2003 | Silvian et al. |
| 6,526,321 B1 | 2/2003 | Spher |
| 6,539,253 B2 | 3/2003 | Thompson et al. |
| 6,545,854 B2 | 4/2003 | Trinh et al. |
| 6,555,745 B1 | 4/2003 | Kruse et al. |
| 6,563,132 B1 | 5/2003 | Talroze et al. |
| 6,566,978 B2 | 5/2003 | Stevenson et al. |
| 6,567,259 B2 | 5/2003 | Stevenson et al. |
| 6,580,947 B1 | 6/2003 | Thompson |
| 6,584,351 B1 | 6/2003 | Ekwall |
| 6,595,756 B2 | 7/2003 | Gray et al. |
| 6,626,937 B1 | 9/2003 | Cox |
| 6,629,938 B1 | 10/2003 | Engvall |
| 6,631,290 B1 | 10/2003 | Guck et al. |
| 6,631,555 B1 | 10/2003 | Youker et al. |
| 6,640,137 B2 | 10/2003 | MacDonald |
| 6,643,903 B2 | 11/2003 | Stevenson et al. |
| 6,646,198 B2 | 11/2003 | Maciver et al. |
| 6,648,914 B2 | 11/2003 | Berrang et al. |
| 6,662,049 B1 | 12/2003 | Miller |
| 6,673,999 B1 | 1/2004 | Wang et al. |
| 6,711,440 B2 | 3/2004 | Deal et al. |
| 6,713,671 B1 | 3/2004 | Wang et al. |
| 6,718,203 B2 | 4/2004 | Weiner et al. |
| 6,718,207 B2 | 4/2004 | Connelly |
| 6,725,092 B2 | 4/2004 | MacDonald et al. |
| 6,731,979 B2 | 5/2004 | MacDonald |
| 6,795,730 B2 | 9/2004 | Connelly et al. |
| 6,901,292 B2 | 5/2005 | Hrdlicka et al. |
| 6,925,328 B2 | 8/2005 | Foster et al. |
| 6,937,906 B2 | 8/2005 | Terry et al. |
| 6,963,779 B1 | 11/2005 | Shankar |
| 7,013,180 B2 | 3/2006 | Villaseca et al. |
| 7,050,855 B2 | 5/2006 | Zeijlemaker et al. |
| 7,076,283 B2 | 7/2006 | Cho et al. |
| 7,082,328 B2 | 7/2006 | Funke |
| 7,092,756 B2 | 8/2006 | Zhang et al. |
| 7,123,013 B2 | 10/2006 | Gray |
| 7,138,582 B2 | 11/2006 | Lessar et al. |
| 7,164,950 B2 | 1/2007 | Kroll et al. |
| 7,174,219 B2 | 2/2007 | Wahlstrand et al. |
| 7,174,220 B1 | 2/2007 | Chitre et al. |
| 7,212,863 B2 | 5/2007 | Strandberg |
| 7,231,251 B2 | 6/2007 | Yonce et al. |
| 7,242,981 B2 | 7/2007 | Ginggen |

| Patent/Publication | Date | Inventor |
|---|---|---|
| 7,369,898 B1 | 5/2008 | Kroll et al. |
| 7,388,378 B2 | 6/2008 | Gray et al. |
| 7,509,167 B2 | 3/2009 | Stessman |
| 7,561,915 B1 | 7/2009 | Cooke et al. |
| 2001/0002000 A1 | 5/2001 | Kumar et al. |
| 2001/0006263 A1 | 7/2001 | Hayward |
| 2001/0011175 A1 | 8/2001 | Hunter et al. |
| 2001/0018123 A1 | 8/2001 | Furumori et al. |
| 2001/0025139 A1 | 9/2001 | Pearlman |
| 2001/0037134 A1 | 11/2001 | Munshi |
| 2001/0050837 A1 | 12/2001 | Stevenson et al. |
| 2002/0019658 A1 | 2/2002 | Munshi |
| 2002/0026224 A1 | 2/2002 | Thompson et al. |
| 2002/0038135 A1 | 3/2002 | Connelly et al. |
| 2002/0050401 A1 | 5/2002 | Youker et al. |
| 2002/0072769 A1 | 6/2002 | Silvian et al. |
| 2002/0102835 A1 | 8/2002 | Stucchi et al. |
| 2002/0116028 A1 | 8/2002 | Greatbatch et al. |
| 2002/0116029 A1 | 8/2002 | Miller et al. |
| 2002/0116033 A1 | 8/2002 | Greatbatch et al. |
| 2002/0116034 A1 | 8/2002 | Miller et al. |
| 2002/0117314 A1 | 8/2002 | Maciver et al. |
| 2002/0128689 A1 | 9/2002 | Connelly et al. |
| 2002/0128691 A1 | 9/2002 | Connelly |
| 2002/0133086 A1 | 9/2002 | Connelly et al. |
| 2002/0133199 A1 | 9/2002 | MacDonald et al. |
| 2002/0133200 A1 | 9/2002 | Weiner et al. |
| 2002/0133201 A1 | 9/2002 | Connelly et al. |
| 2002/0133202 A1 | 9/2002 | Connelly et al. |
| 2002/0133208 A1 | 9/2002 | Connelly |
| 2002/0133211 A1 | 9/2002 | Weiner et al. |
| 2002/0133216 A1 | 9/2002 | Connelly et al. |
| 2002/0138102 A1 | 9/2002 | Weiner et al. |
| 2002/0138107 A1 | 9/2002 | Weiner et al. |
| 2002/0138108 A1 | 9/2002 | Weiner et al. |
| 2002/0138110 A1 | 9/2002 | Connelly et al. |
| 2002/0138112 A1 | 9/2002 | Connelly et al. |
| 2002/0138113 A1 | 9/2002 | Connelly et al. |
| 2002/0138124 A1 | 9/2002 | Helfer et al. |
| 2002/0143258 A1 | 10/2002 | Weiner et al. |
| 2002/0147388 A1 | 10/2002 | Mass et al. |
| 2002/0147470 A1 | 10/2002 | Weiner et al. |
| 2002/0162605 A1 | 11/2002 | Horton, Jr. et al. |
| 2002/0166618 A1 | 11/2002 | Wolf et al. |
| 2002/0175782 A1 | 11/2002 | Trihn et al. |
| 2002/0183796 A1 | 12/2002 | Connelly |
| 2002/0198569 A1 | 12/2002 | Foster et al. |
| 2003/0036774 A1 | 2/2003 | Maier et al. |
| 2003/0036776 A1 | 2/2003 | Foster et al. |
| 2003/0045907 A1 | 3/2003 | MacDonald |
| 2003/0053284 A1 | 3/2003 | Stevenson et al. |
| 2003/0055457 A1 | 3/2003 | MacDonald |
| 2003/0056820 A1 | 3/2003 | MacDonald |
| 2003/0074029 A1 | 4/2003 | Deno et al. |
| 2003/0081370 A1 | 5/2003 | Haskell et al. |
| 2003/0083570 A1 | 5/2003 | Cho et al. |
| 2003/0083723 A1 | 5/2003 | Wilkinson et al. |
| 2003/0083726 A1 | 5/2003 | Zeijlemaker et al. |
| 2003/0083728 A1 | 5/2003 | Greatbatch et al. |
| 2003/0100925 A1 | 5/2003 | Pape et al. |
| 2003/0109901 A1 | 6/2003 | Greatbatch |
| 2003/0111142 A1 | 6/2003 | Horton, Jr. et al. |
| 2003/0114897 A1 | 6/2003 | Von Arx et al. |
| 2003/0114898 A1 | 6/2003 | Von Arx et al. |
| 2003/0120197 A1 | 6/2003 | Kaneko et al. |
| 2003/0130647 A1 | 7/2003 | Gray et al. |
| 2003/0130700 A1 | 7/2003 | Miller et al. |
| 2003/0130701 A1 | 7/2003 | Miller |
| 2003/0130708 A1 | 7/2003 | Von Arx et al. |
| 2003/0135114 A1 | 7/2003 | Pacetti |
| 2003/0135160 A1 | 7/2003 | Gray et al. |
| 2003/0139096 A1 | 7/2003 | Stevenson et al. |
| 2003/0140931 A1 | 7/2003 | Zeijlemaker et al. |
| 2003/0144704 A1 | 7/2003 | Terry et al. |
| 2003/0144705 A1 | 7/2003 | Funke |
| 2003/0144706 A1 | 7/2003 | Funke |
| 2003/0144716 A1 | 7/2003 | Reinke et al. |
| 2003/0144717 A1 | 7/2003 | Hagele |
| 2003/0144718 A1 | 7/2003 | Zeijlemaker |
| 2003/0144719 A1 | 7/2003 | Zeijlemaker |
| 2003/0144720 A1 | 7/2003 | Villaseca et al. |
| 2003/0144721 A1 | 7/2003 | Villaseca et al. |
| 2003/0149459 A1 | 8/2003 | Von Arx et al. |
| 2003/0158584 A1 | 8/2003 | Cates et al. |
| 2003/0176900 A1 | 9/2003 | MacDonald |
| 2003/0179536 A1 | 9/2003 | Stevenson et al. |
| 2003/0191505 A1 | 10/2003 | Gryzwa et al. |
| 2003/0195570 A1 | 10/2003 | Deal et al. |
| 2003/0199755 A1 | 10/2003 | Halperin et al. |
| 2003/0204207 A1 | 10/2003 | MacDonald et al. |
| 2003/0204215 A1 | 10/2003 | Gunderson et al. |
| 2003/0204217 A1* | 10/2003 | Greatbatch ............... 607/36 |
| 2003/0213604 A1 | 11/2003 | Stevenson et al. |
| 2003/0213605 A1 | 11/2003 | Brendel et al. |
| 2004/0005483 A1 | 1/2004 | Lin |
| 2004/0015162 A1 | 1/2004 | McGaffigan |
| 2004/0015197 A1 | 1/2004 | Gunderson |
| 2004/0019273 A1 | 1/2004 | Helfer et al. |
| 2004/0088012 A1 | 5/2004 | Kroll et al. |
| 2004/0093432 A1 | 5/2004 | Luo et al. |
| 2005/0070975 A1 | 3/2005 | Zeijlemaker et al. |
| 2005/0113676 A1 | 5/2005 | Weiner et al. |
| 2005/0113873 A1 | 5/2005 | Weiner et al. |
| 2005/0113876 A1 | 5/2005 | Weiner et al. |
| 2005/0222656 A1 | 10/2005 | Wahlstrand et al. |
| 2005/0222657 A1 | 10/2005 | Wahlstrand et al. |
| 2005/0222658 A1 | 10/2005 | Hoegh et al. |
| 2005/0222659 A1 | 10/2005 | Olsen et al. |
| 2006/0025820 A1 | 2/2006 | Phillips et al. |
| 2006/0030774 A1 | 2/2006 | Gray et al. |
| 2006/0041294 A1 | 2/2006 | Gray |
| 2006/0167496 A1 | 7/2006 | Nelson et al. |
| 2006/0247747 A1 | 11/2006 | Olsen et al. |
| 2006/0247748 A1 | 11/2006 | Wahlstrand et al. |
| 2006/0271138 A1 | 11/2006 | MacDonald |
| 2006/0293591 A1 | 12/2006 | Wahlstrand et al. |
| 2007/0021814 A1 | 1/2007 | Inman et al. |
| 2007/0179577 A1 | 8/2007 | Marshall et al. |
| 2007/0179582 A1 | 8/2007 | Marshall et al. |
| 2007/0191914 A1 | 8/2007 | Stessman |
| 2007/0203523 A1 | 8/2007 | Betzold |
| 2007/0238975 A1 | 10/2007 | Zeijlemaker |
| 2007/0255332 A1* | 11/2007 | Cabelka et al. ............. 607/37 |
| 2008/0033497 A1 | 2/2008 | Bulkes et al. |
| 2008/0132985 A1 | 6/2008 | Wedan et al. |
| 2008/0221638 A1* | 9/2008 | Wedan et al. ............... 607/34 |
| 2009/0138058 A1 | 5/2009 | Cooke et al. |
| 2009/0149909 A1 | 6/2009 | Ameri |
| 2009/0204182 A1 | 8/2009 | Ameri |
| 2009/0210025 A1 | 8/2009 | Ameri |
| 2010/0087892 A1 | 4/2010 | Stubbs et al. |
| 2010/0211123 A1 | 8/2010 | Stubbs et al. |

FOREIGN PATENT DOCUMENTS

| | | |
|---|---|---|
| EP | 0591334 | 4/1994 |
| EP | 0705621 | 4/1996 |
| EP | 0719570 | 7/1996 |
| EP | 0836413 | 4/1998 |
| EP | 0331959 | 9/1998 |
| EP | 0870517 | 10/1998 |
| EP | 0891207 | 1/1999 |
| EP | 0891786 | 1/1999 |
| EP | 0980105 | 2/2000 |
| EP | 0989623 | 3/2000 |
| EP | 0989624 | 3/2000 |
| EP | 1007132 | 6/2000 |
| EP | 1007140 | 6/2000 |
| EP | 1060762 | 12/2000 |
| EP | 1061849 | 12/2000 |
| EP | 1109180 | 6/2001 |
| EP | 1128764 | 9/2001 |
| EP | 1191556 | 3/2002 |
| EP | 1271579 | 1/2003 |
| EP | 1308971 | 5/2003 |
| EP | 1372782 | 1/2004 |
| WO | WO 91/04069 | 4/1991 |
| WO | WO 96/38200 | 12/1996 |
| WO | WO 97/12645 | 4/1997 |

| WO | WO 00/54953 | 9/2000 |
| WO | WO 01/37286 | 5/2001 |
| WO | WO 01/80940 | 11/2001 |
| WO | WO 01/86774 | 11/2001 |
| WO | WO 02/056761 | 7/2002 |
| WO | WO 02/065895 | 8/2002 |
| WO | WO 02/072004 | 9/2002 |
| WO | WO 02/089665 | 11/2002 |
| WO | WO 02/092161 | 11/2002 |
| WO | WO 03/013199 | 2/2003 |
| WO | WO 03/037399 | 5/2003 |
| WO | WO 03/059445 | 7/2003 |
| WO | WO 03/061755 | 7/2003 |
| WO | WO 03/063946 | 8/2003 |
| WO | WO 03/063952 | 8/2003 |
| WO | WO 03/063954 | 8/2003 |
| WO | WO 03/063955 | 8/2003 |
| WO | WO 03/063956 | 8/2003 |
| WO | WO 03/063958 | 8/2003 |
| WO | WO 03/063962 | 8/2003 |
| WO | WO 03/070098 | 8/2003 |
| WO | WO 03/073449 | 9/2003 |
| WO | WO 03/073450 | 9/2003 |
| WO | WO 03/086538 | 10/2003 |
| WO | WO 03/090846 | 11/2003 |
| WO | WO 03/090854 | 11/2003 |
| WO | WO 03/095022 | 11/2003 |
| WO | WO 2006/124481 | 11/2006 |

OTHER PUBLICATIONS

Luechinger, Roger et al., "In vivo heating of pacemaker leads during magnetic resonance imaging", *European Heart Journal* 2005;26:376-383.

Shellock, Frank G. et al., "Cardiovascular catheters and accessories: ex vivo testing of ferromagnetism, heating, and artifacts associated with MRI", *Journal of Magnetic Resonance Imaging*, Nov./Dec. 1998; 8:1338-1342.

Shellock FG, "Reference manual for magnetic resonance safety, implants, and devices", pp. 136-139, 2008 ed. Los Angeles; Biomedical Research Publishing Group; 2008.

Kerr, Martha, Shock Rate Cut 70% With ICDs Programmed to First Deliver Antitachycardia Pacing: Results of the PainFREE Rx II Trial, Medscape CRM News, May 21, 2003.

Schueler et al., "MRI Compatibility and Visibility Assessment of Implantable Medical Devices", Journal of Magnetic Resonance Imaging, 9:596-603 (1999).

Sweeney, Michael O. et al., Appropriate and Inappropriate Ventricular Therapies, Quality of Life, and Mortality Among Primary and Secondary Prevention Implantable Cardioverter Defibrillator Patients: Results From the Pacing Fast VT REduces Shock ThErapies (PainFREE Rx II) Trial, American Heart Association, 2005.

Wilkoff, Bruce L. et al., "A Comparison of Empiric to Physician-Tailored Programming of Implantable Cardioverter-Defibrillators Results From the Prospective Randomized Multicenter EMPIRIC Trial," Journal of the American College of Cardiology, vol. 48, No. 2, 2006. doi:10.1016/j.jacc.2006.03.037.

* cited by examiner

US 8,032,228 B2

METHOD AND APPARATUS FOR DISCONNECTING THE TIP ELECTRODE DURING MRI

CROSS REFERENCE TO RELATED APPLICATION

The present application claims priority under 35 U.S.C. §119(e) to U.S. Provisional Patent No. 60/992,991, filed on Dec. 6, 2007, the entire contents of which are incorporated herein by reference.

TECHNICAL FIELD

Embodiments of the present invention relate to medical devices and the simultaneous delivery of diagnostic and therapeutic treatments. More specifically, embodiments of the present invention relate to devices and methods for delivering cardiovascular diagnostic, pacing therapy in a magnetic field environment, or Tachy shock therapy.

BACKGROUND

Magnetic resonance imaging (MRI) is a non-invasive imaging method that utilizes nuclear magnetic resonance techniques to render images within a patient's body. Typically, MRI systems employ the use of a magnetic coil having a magnetic field strength of between about 0.2 to 3 Teslas. During the procedure, the body tissue is briefly exposed to RF pulses of electromagnetic energy in a plane perpendicular to the magnetic field. The resultant electromagnetic energy from these pulses can be used to image the body tissue by measuring the relaxation properties of the excited atomic nuclei in the tissue.

During imaging, the electromagnetic radiation produced by the MRI system may be picked up by implantable device leads used in implantable medical devices such as pacemakers or cardiac defibrillators. This energy may be transferred through the lead to the electrode in contact with the tissue, which may lead to elevated temperatures at the point of contact. The degree of tissue heating is typically related to factors such as the length of the lead, the properties of the tissue near the lead, the conductivity or impedance of the lead, the shape of the lead, and the surface area of the lead electrodes. Exposure to a magnetic field may also induce an undesired voltage in the lead.

SUMMARY

The present invention relates to devices and methods for delivering cardiovascular diagnostic, shock, or pacing therapy in a magnetic field environment. According to some embodiments, a medical device includes a pulse generator, an electrode configured to contact tissue in a body vessel, and a lead. The lead includes a lead conductor connecting the pulse generator with the electrode via first and second conductive paths. The first conductive path is parallel to the second conductive path. The medical device includes a first switch electrically coupled in series between the lead conductor and the electrode. The first switch includes a non-conductive state in the presence of the magnetic field, the non-conductive state preventing the formation of the first conductive path between the pulse generator and the electrode. The first switch includes a conductive state in the absence of the magnetic field, the conductive state establishing the conductive path between the pulse generator and the electrode.

The medical device further includes a second switch electrically connected in series between the lead conductor and the electrode. The second switch includes a non-conductive state that prevents the second conductive path between the pulse generator and the electrode. The second switch includes a conductive state that establishes the second conductive path between the pulse generator and the electrode upon reception of a voltage applied across the second switch which exceeds a threshold voltage. The first switch in the non-conductive state and the second switch in the non-conductive state electrically shields the electrode from electromagnetic radiation and induced voltages during magnetic resonance imaging.

While some embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
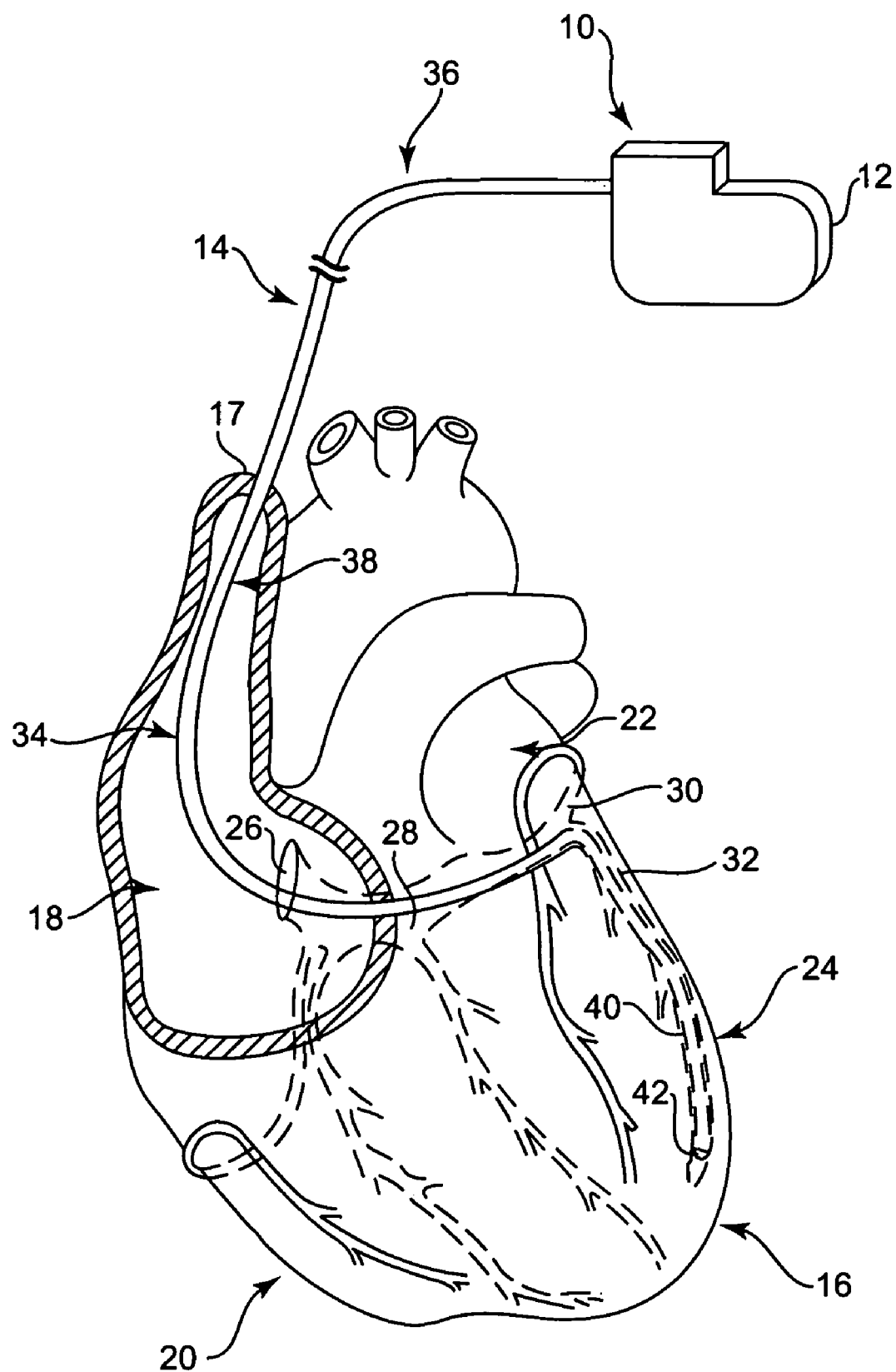
FIG. 1 is a schematic drawing of an example cardiac rhythm management system including a pulse generator coupled to a lead deployed in a patient's heart.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the present disclosure.

DETAILED DESCRIPTION

FIG. 1 is a schematic drawing of a cardiac rhythm management system 10 including a pulse generator 12 coupled to a lead 14 deployed in a patient's heart 16. As is known in the art, the pulse generator 12 is typically implanted subcutaneously at an implantation location in the patient's chest or abdomen. As shown, the heart 16 includes a superior vena cava 17, a right atrium 18 and a right ventricle 20, a left atrium 22 and a left ventricle 24, a coronary sinus ostium 26, a coronary sinus 28, and various cardiac branch vessels including a great cardiac vein 30 and an exemplary branch vessel 32.

In the embodiment of FIG. 1, the lead 14 may include an elongated body 34 having a proximal region 36 and a distal region 38. The distal region 38 has a distal end 40 including an electrode 42. The lead 14 includes a lead conductor which electrically connects the pulse generator 12 to the electrode 42. To facilitate left ventricular pacing epicardially via an epicardial approach, the lead 14 may be deployed in coronary veins 32 through the coronary sinus 28. In embodiments, the lead 14 can be implanted in other locations of the body such as the right ventricle 20, right atrium 18, or any other desired location in the body. Although FIG. 1 depicts the lead 14 as part of a cardiac rhythm management system 10 with an electrode 42, the lead 14 may alternatively include one or more sensors and/or one or more electrodes 42, and may couple the one or more sensors or electrodes 42 with a monitor in addition to, or in lieu of, the pulse generator 12. Additionally, although only one lead is illustrated in FIG. 1, the cardiac management system 10 may include any desired number of leads.

In embodiments, the pulse generator 12 is configured to emit therapy pulses such as pacing pulses for cardiovascular therapy or pulses for shock therapy. Examples of therapy pulses include, but are not limited to, cardiac pacing pulses for heart failure and bradycardia; anti-tachy pacing and shock therapy for tachycardia; and pacing pulses for neurostimulation and pain mitigation. In embodiments, the pulse generator 12 operates in a normal mode in the absence of a magnetic field and an MRI mode in the presence of the magnetic field generated during MRI imaging. In embodiments, the pulse generator 12 includes one or more sensors to detect the presence of the magnetic field. In some embodiments, the pulse generator 12 is communicable with a remote device that switches the pulse generator 12 between the normal and MRI modes. In other embodiments, the pulse generator 12 detects the presence of a magnetic field by measuring the lead impedance of the lead conductor of lead 14.

In some embodiments, and as discussed further herein, when the pulse generator 12 is operating in the normal mode, the pulse generator 12 emits pacing pulses at a specified voltage level. When the pulse generator 12 is operating in the MRI mode, the pulse generator 12 emits pacing pulses at the specified voltage level plus a threshold voltage. In embodiments, the pulse generator 12 operates in the MRI mode only upon detection of the magnetic field. Generally, the pulse generator 12 is in the presence of the magnetic field for a minimal portion of the life time of the battery of the pulse generator 12. Accordingly, configuring the pulse generator 12 to operate in the MRI mode only when needed or in the presence of a magnetic field conserves the battery power of the pulse generator 12 since the pulse generator 12 operating in the MRI mode may consume more battery power compared to operating in the normal mode.

Figure 2A:
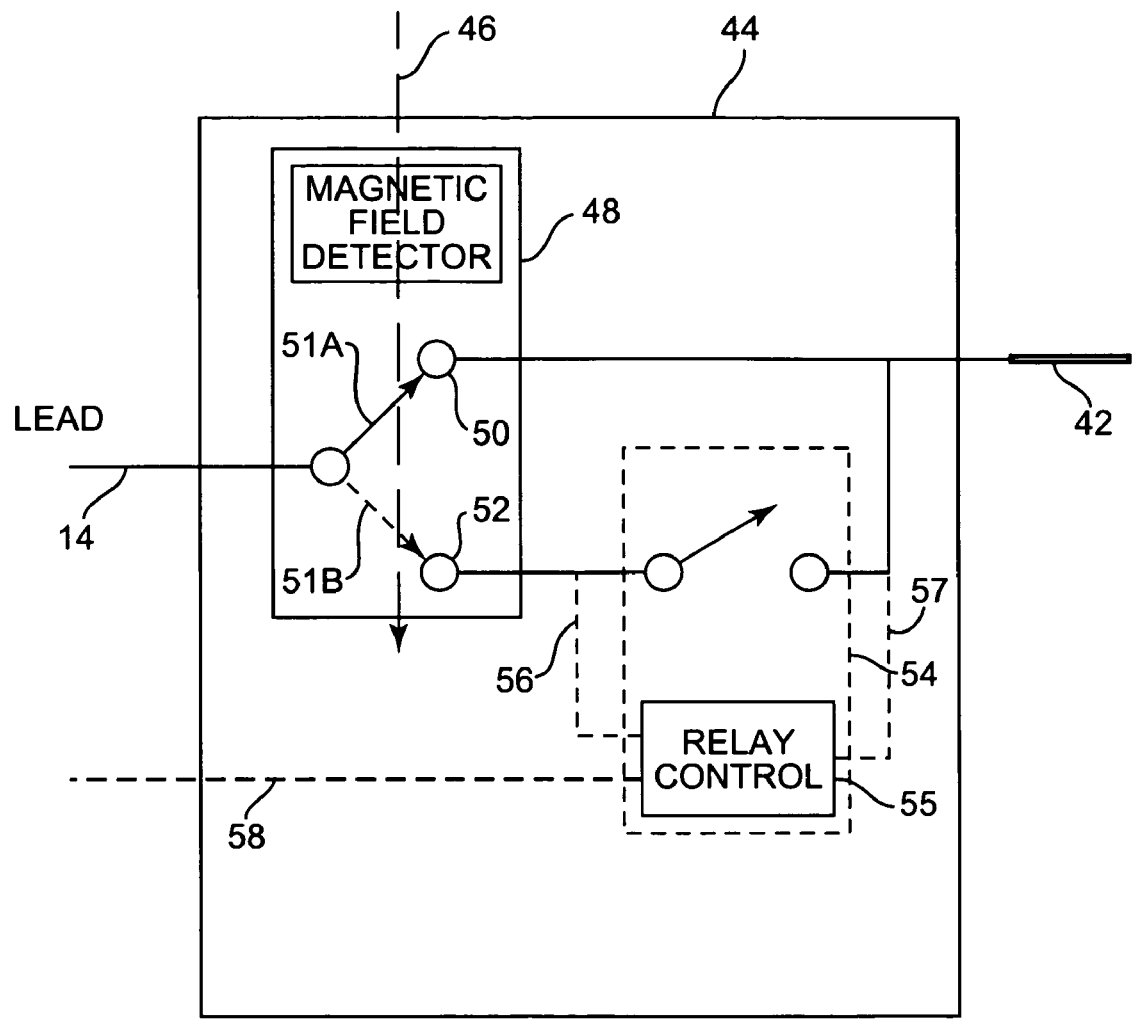
FIG. 2A illustrates an MRI electrode isolation device between a lead conductor and an electrode.

FIG. 2A illustrates an MRI electrode isolation device 44 between a lead 14 and an electrode 42, according to embodiments of the present invention. In embodiments, the isolation device 44 is used to isolate the electrode (and thus surrounding tissue) from electromagnetic radiation, induced currents or voltages caused by the MRI procedure, and/or interaction with the elongated lead 14 conductors.

In embodiments, the device 44 includes a magnetic switch 48. In embodiments, the magnetic switch 48 is a single-pole double throw switch such as a reed switch. In the absence of any magnetic field, the switch 48, which is normally closed, shorts the lead conductor and the electrode at node 50 to conserve energy. In the presence of a magnetic field of the magnitude typically observed in an MRI procedure, such as the static magnetic field represented by arrow 46 of FIG. 2A, the switch 48 opens and redirects the circuit path through node 52 and through a relay control switch 54. In embodiments, the relay control switch 54 is normally open to isolate the electrode (and thus surrounding tissue) from the elongated lead 14 conductor, electromagnetic radiation and/or induced currents or voltages caused by the MRI procedure. Further, in embodiments, the relay control switch 54 is configured to close the circuit between the lead conductor and the electrode 42 during the delivery of required therapy (e.g. a pacing pulse), according to some embodiments.

According to some embodiments, the relay control switch 54 includes a relay control 55 that monitors the voltage across the switch 54 and closes the switch 54 when a certain threshold voltage level has been exceeded. According to embodiments, the therapy voltage provided by the pulse generator 12, when operating in the MRI mode, exceeds the threshold voltage level across the relay control switch 54, and the relay control switch 54 closes during the therapy pulse, which establishes a conductive path between the pulse generator 12 and lead 14 and electrode 42 via node 52. In some embodiments, the relay control 55 utilizes lines 56 and 57 to determine the voltage across switch 54 by measuring the voltage potential between node 51B and the electrode 42. If this voltage potential exceeds the threshold, the relay control 55 triggers the closure of the relay control switch 54. According to other embodiments, the pulse generator 12 is configured to send a control signal via line 58 timed to coincide with a therapy pulse, in order to trigger closure of the relay control switch 54 during the therapy pulse.

The magnetic switch 48 may be a mechanical switch according to embodiments. In some embodiments, the switch 48 can monitor a signal from a magnetic field detector and/or sensor and change the state of the switch 48 upon detection of a magnetic field 46. Alternatively, and in other embodiments, the switch 48 itself may be sensitive to the magnetic field. As an example, the switch 48 may be a reed switch, in which the magnetic field 46 itself moves the pole from the position shown in FIG. 2A in solid lines (arrow 51A connected to node 50) to the position shown in FIG. 2A in dashed lines (arrow 51B connected to node 52).

Figure 2B:
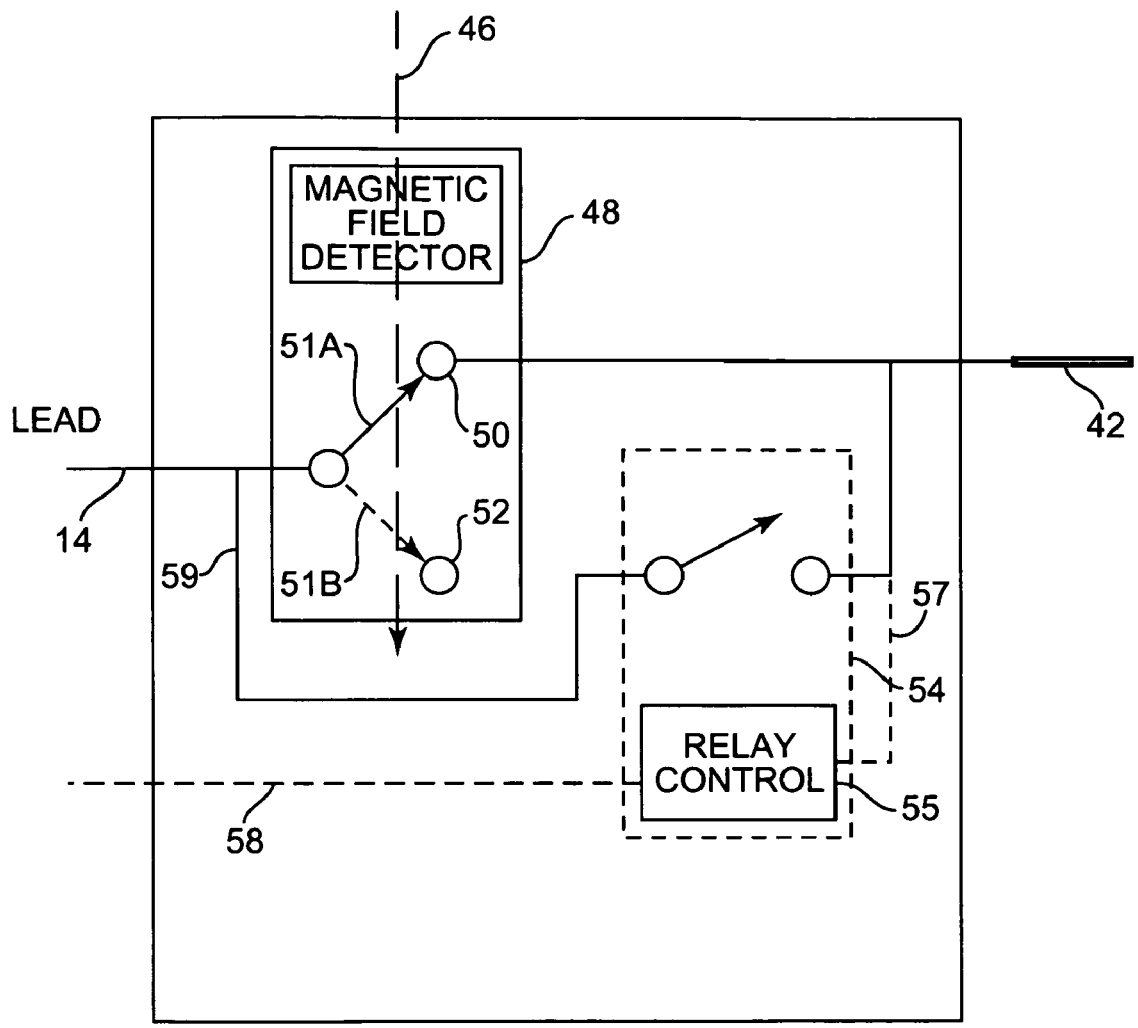
FIG. 2B illustrates an alternative configuration of the MRI electrode isolation device between the lead conductor and the electrode.

FIG. 2B illustrates an alternative configuration of the MRI electrode isolation device between the lead conductor and the electrode. As illustrated in FIG. 2B, the relay control switch 54 is directly connected to the lead 14 via line 59. In embodiments, the line 59 is an extension of the lead 14 providing a connection between the lead 14 and the relay control switch 54. Accordingly, in this configuration, in the absence of the magnetic field 46, the switch 48 shorts the lead 14 and the electrode 42 at node 50. In the presence of the magnetic field 46, the pole of switch 48 moves from node 50 to node 52 disconnecting the lead 14 from the electrode 42. In the presence of the magnetic field 46, during delivery of a therapy pulse, the pulse generator 12 sends a signal to the relay control 55 via line 58 to close the switch 54. Accordingly, therapy pulses sent from the pulse generator 12 along lead 14 reach the electrode via line 59 and the relay control switch 54.

Figure 3:
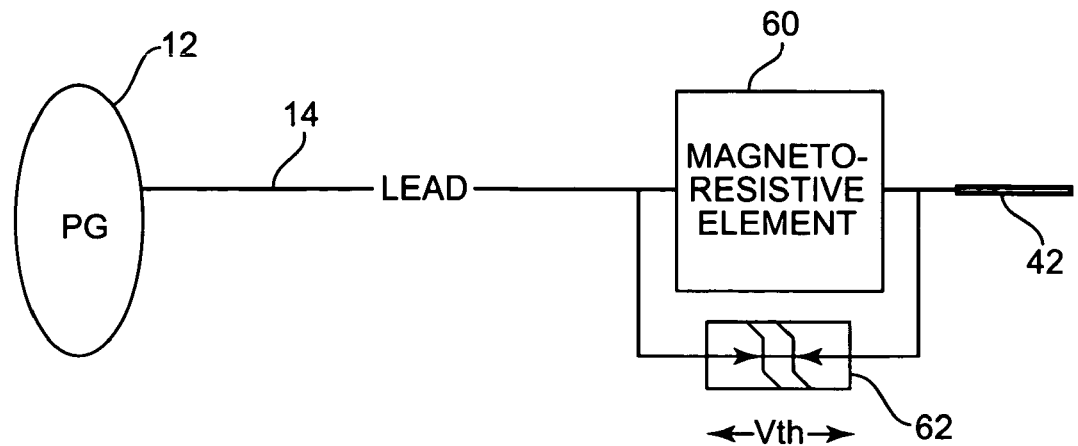
FIG. 3 illustrates a pulse generator with a lead having an electrode separated from the lead conductor by a magnetoresistive element with a bypass circuit.

FIG. 3 illustrates a pulse generator 12 with a lead 14 having an electrode 42 separated from the lead conductor by a magnetoresistive element 60 with a bypass circuit 62, according to embodiments of the present invention. The magnetoresistive element 60 may be, for example, ballistic magnetoresistive ("BMR") material which greatly increases the resistance between the lead conductor and the electrode 42 in the presence of a static magnetic field produced by an MRI scanner. According to some embodiments, the resistance created by the magnetoresistive element 60 in the presence of an MRI static magnetic field is large enough to prevent formation of the conductive path between the pulse generator 12 and the electrode 42 via the magnetoresistive element 60. Alternatively, and in other embodiments, the magnetoresistive element 60 may be a magnetic switch as described above with respect to FIGS. 2A and 2B.

A bypass device 62 may be used to bypass the magnetoresistive element 60 in the presence of a magnetic field. The bypass device 62 may be an electrical or mechanical threshold circuit, such as, for example, a Zener diode, back-to-back Zener diodes, or devices with similar characteristics. According to some embodiments, the bypass device 62 features an open circuit or a high resistance until a voltage applied across the device 62 exceeds a threshold voltage. In embodiments, the pulse generator 12, when operating in the MRI mode, is configured to deliver a pacing pulse with a voltage level that exceeds the threshold voltage of the device 62.

Figure 4:
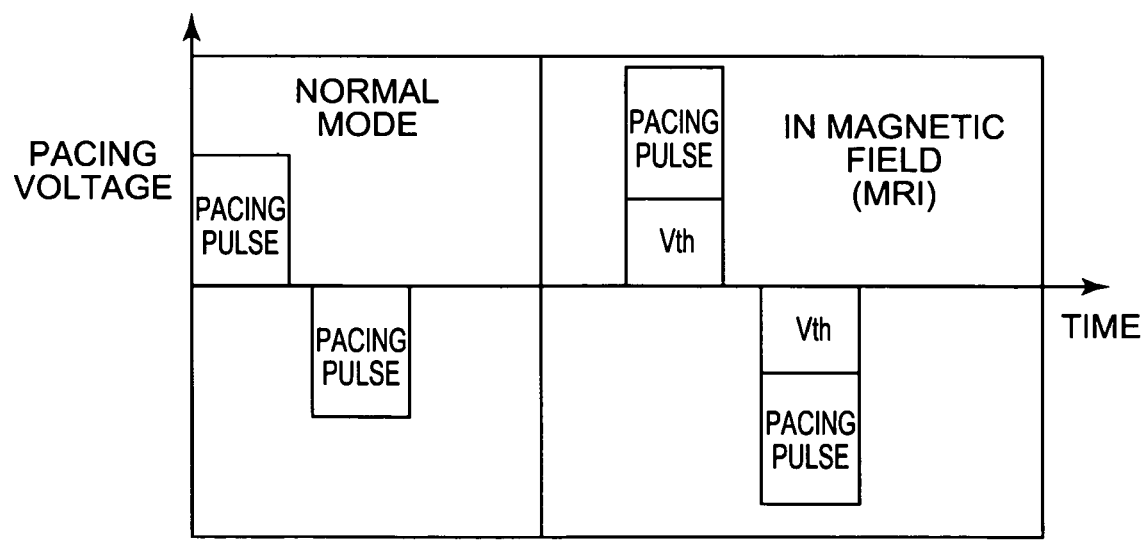
FIG. 4 is a chart which illustrates pacing voltage pulse magnitudes in both the normal mode and the MRI mode.

FIG. 4 is a chart which illustrates pacing voltage pulse magnitudes verses time in both the normal mode and the MRI mode. In the normal mode when an MRI magnetic field is not present, the pulse generator 12 may supply pacing pulses of a certain magnitude, as shown on the left side of FIG. 4. In the MRI mode when the MRI magnetic field is detected, the pulse generator 12 supplies pacing pulses of a magnitude equal to the normal magnitude plus a threshold voltage, as shown on the right side of FIG. 4. In embodiments, the pacing pulse+Vth is sufficient to override the bypass device 62 permitting a conductive path between the pulse generator 12 and the electrode 42. In embodiments, the Vth is removed from the pacing pulse by the bypass device 62 to provide a pacing pulse of normal voltage level to the electrode 42 and surrounding tissue. Accordingly, the pacing pulse+Vth in the MRI mode permits the pacing pulse to override the bypass device 62 with the threshold voltage level and permits delivery of a pacing pulse of normal magnitude to the electrode 42.

In embodiments, the duration of pacing pulses and signals emitted from the pulse generator 12 are longer than a threshold duration, which means that the frequency of the pacing pulses is not higher than a threshold frequency (e.g., frequency=1/duration). In some embodiments, the threshold duration is 60 nanoseconds and the threshold frequency is 8.5 MHz. In embodiments, any switch, controller, or device that receives pacing pulses or signals from the pulse generator 12 is responsive to pacing pulses or signals below a particular frequency. As an example, the bypass device 62 (FIG. 3) closes upon receiving one or more pacing pulses from the pulse generator 12 that are above the threshold voltage and have a duration longer than the threshold duration.

Figure 5A:
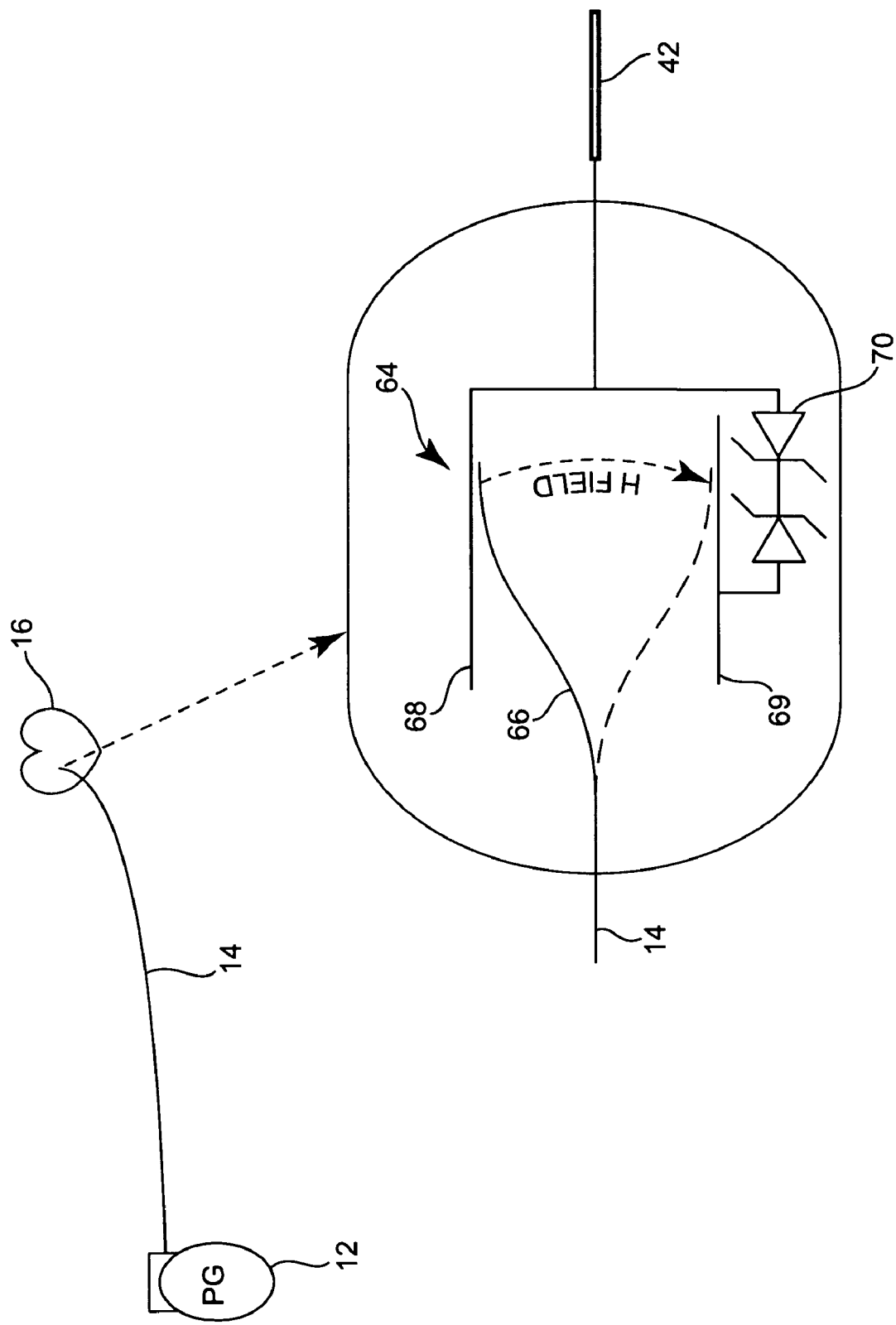
FIG. 5A illustrates a pulse generator and a lead with an enlarged view of a hermetically sealed reed switch and double Zener bypass.

FIG. 5A illustrates a pulse generator 12 and a lead 14 implanted within the heart 16, with an enlarged view of a hermetically sealed reed switch 64 and double Zener bypass 70, according to embodiments of the present invention. In embodiments, the switch 64 includes a pole 66, a non-ferromagnetic contact 68, and a ferromagnetic contact 69. The pole 66 of the switch 64, which is in electrical communication with the lead conductor of the lead 14, may be constructed with a ferromagnetic material. In further embodiments, the pole 66 is elastic. In the absence of a magnetic field, the pole 66 is in a non-expanded state (e.g. relaxed state) and keeps in contact with the non-ferromagnetic contact 68. When applying a magnetic field to the switch 64, such as that applied during an MRI procedure, the ferromagnetic pole 66 is attracted to the ferromagnetic contact 69. Accordingly, in the presence of the magnetic field, the attraction between the pole 66 and the ferromagnetic contact 69 causes the pole 66 to move towards the ferromagnetic contact 69. Thus, in the presence of the magnetic field, the pole 66 is deflected from the position shown in FIG. 5A in solid lines in which the lead conductor is shorted to the electrode 42 to the position shown in FIG. 5A in dashed lines in which a back-to-back Zener diode 70 separates the lead conductor from the electrode 42.

The diode 70 may be used to override the switch 64 during therapy. In embodiments, the pulse generator 12, when operating in the MRI mode, is configured to deliver a pacing pulse such as the pacing pulse illustrated in FIG. 4 with a voltage level high enough to override the back-to-back Zener diode 70.

Figure 5B:
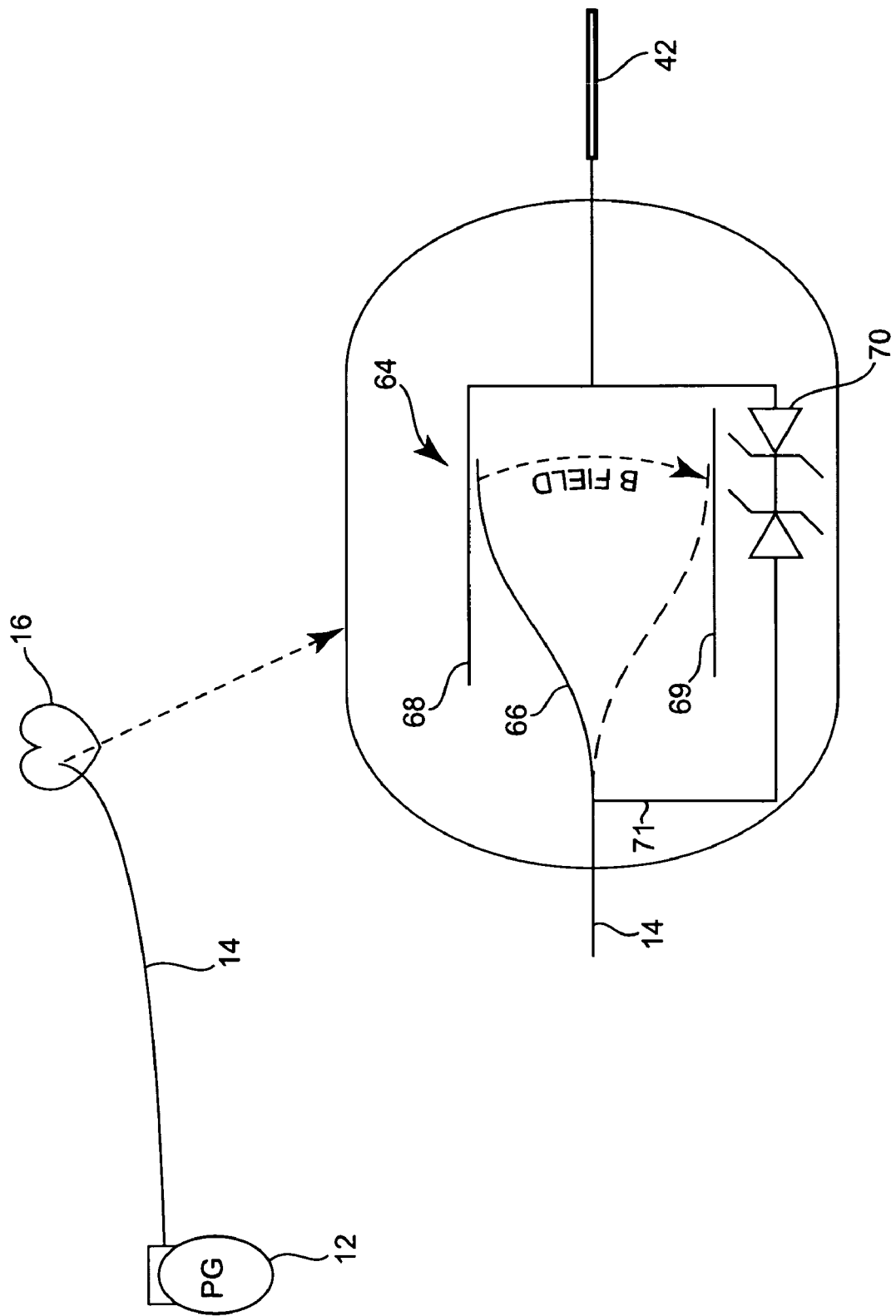
FIG. 5B illustrates an alternative configuration of the pulse generator and the lead with the enlarged view of the hermetically sealed reed switch and double Zener bypass.

FIG. 5B illustrates an alternative configuration of the pulse generator 12 and the lead 14 with the enlarged view of the hermetically sealed reed switch 64 and double Zener bypass 70. The double Zener bypass 70 is directly connected to the lead 14 via line 71. In embodiments, the line 71 is an extension of the lead 14 providing a connection between the lead 14 and the double Zener bypass 70. Accordingly, in this configuration, in the absence of a magnetic field, the pole 66 is in a non-expanded state and keeps in contact with the non-ferromagnetic contact 68. In the presence of the magnetic field, the attraction between the pole 66 and the ferromagnetic contact 69 causes the pole 66 to move towards the ferromagnetic contact 69, which disconnects the lead 14 from the electrode 42. When operating in the MRI mode in the presence of the magnetic field, the pulse generator 12 is configured to emit a therapy pulse with a voltage level high enough to override the back-to-back Zener diode 70 providing a conductive path between the pulse generator 12 and the electrode 42.

Figure 6:
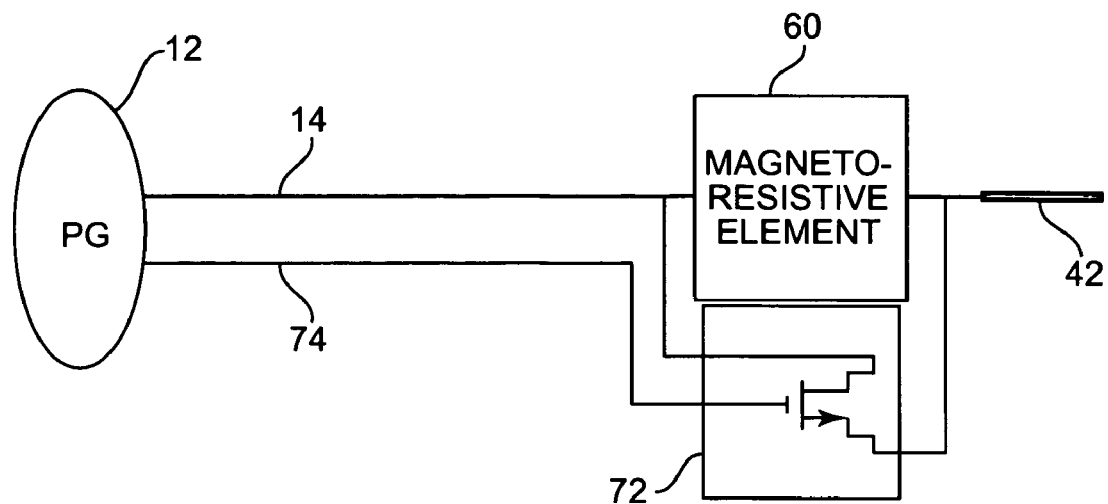
FIG. 6 illustrates a pulse generator with a lead and a magnetoresistive material or reed switch separating the lead conductor and the electrode along with a bypass switch.

FIG. 6 illustrates a pulse generator 12 with a lead 14 and a magnetoresistive element 60 separating the lead conductor and the electrode 42 along with a bypass switch 72. In other embodiments a reed switch separates the lead conductor from the electrode 42. As shown in FIG. 6, the bypass switch 72 is electronically controlled by the pulse generator 12 via a control line 74. In the presence of a magnetic field, the magnetoresistive element 60 changes from a low impedance state to a high impedance state, and substantially electrically isolates the lead conductor of the lead 14 from the electrode 42. A signal sent from the pulse generator 12 to the bypass switch 72 through the control line 74 bypasses the magnetoresistive element 60 during the delivery of therapy pulses. In some embodiments, the bypass signal from the pulse generator 12 is sent through control line 74 to bypass switch 72 during a therapy pulse only when the pulse generator 12 is operating in the MRI mode in order to conserve the battery power of the pulse generator 12. Alternatively, and in other embodiments, the bypass signal from the pulse generator 12 may be sent through control line 74 to bypass switch 72 at other times such as immediately prior to delivering a therapeutic pulse. In embodiments, the control line 74 is a fiber optic line and the switch 72 is an optical switch.

Figure 7:
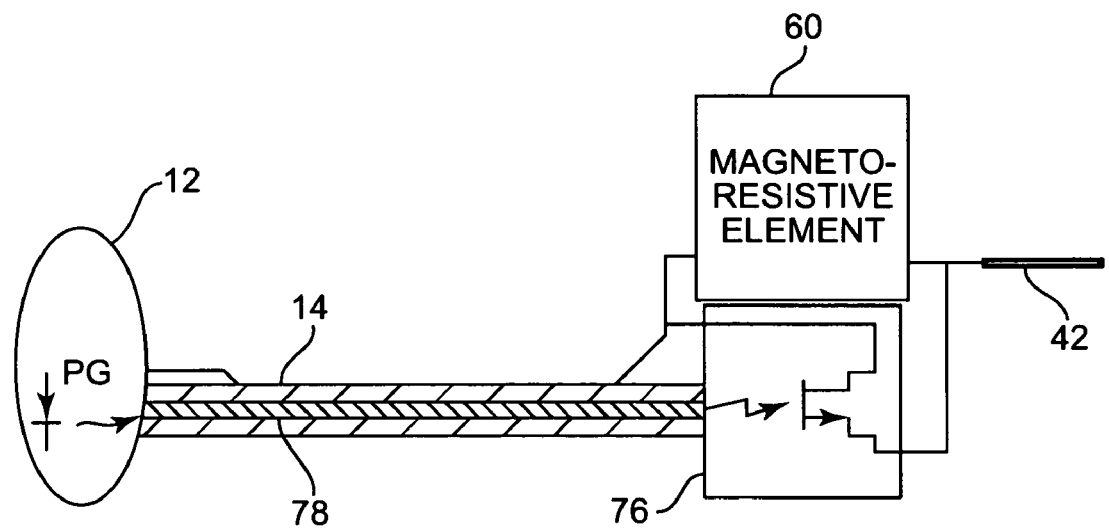
FIG. 7 illustrates a pulse generator with a lead and a magnetoresistive material or reed switch separating the lead conductor and the electrode along with a bypass switch.

FIG. 7 illustrates a pulse generator 12 with a lead 14 and a magnetoresistive element 60 separating the lead conductor and the electrode 42 along with a bypass switch 76. In other embodiments a reed switch separates the lead conductor from the electrode 42. As shown in FIG. 7, the bypass switch 76 is optically controlled by the pulse generator 12 via a fiber optic line 78 located within the lead 14. In embodiments, the fiber optic line 78 may be contained within the lead 14 and connects the pulse generator 12 to the magnetoresistive element. In embodiments, the lead 14 connects the pulse generator 12 to the bypass switch 76.

In the presence of a magnetic field, the magnetoresistive element 60 changes from a low impedance state to a high impedance state, and substantially electrically isolates the lead conductor of the lead 14 from the electrode 42. In embodiments, when the pulse generator 12 is operating in the MRI mode, a signal sent from the pulse generator 12 to the bypass switch 76 via the fiber optic line 78 bypasses the magnetoresistive element 60 during the delivery of therapeutic pulses. Accordingly, while in the MRI mode, the pulse generator 12 activates the bypass switch 76 via fiber optic line 78 to permit therapy pulses to reach the electrode 42 via lead 14. In some embodiments, the bypass signal from the pulse generator 12 is sent through the line 78 to bypass switch 76 during a therapy pulse only when the pulse generator 12 is operating in the MRI mode in order to minimize energy use. By activating the bypass switches 72, 76 only in an MRI environment (e.g., when the pulse generator 12 is operating in an MRI mode) and only during delivery of therapy, the pulse generator 12 may conserve battery power usage.

Figure 8:
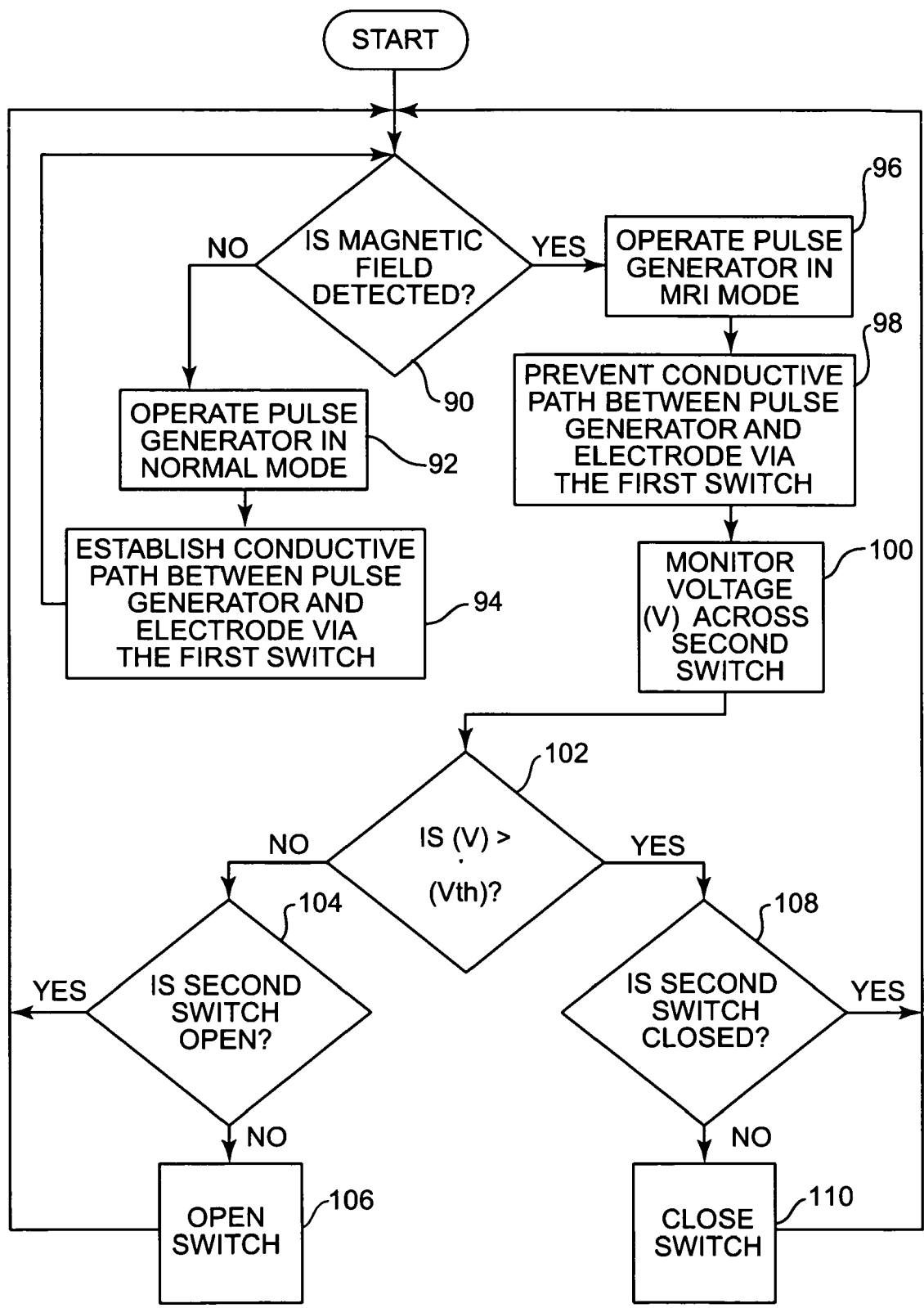
FIG. 8 is an example process for detecting a magnetic field and establishing conductive paths between the pulse generator and the electrode.

FIG. 8 is an example process for detecting a magnetic field and establishing conductive paths between the pulse generator and the electrode. In some embodiments, the process illustrated in FIG. 8 may be applicable to the embodiments disclosed in FIGS. 2, 3, and 5-7. For illustrative purposes, the description of the process in FIG. 8 is made with respect to the embodiment illustrated in FIG. 2A where the single-pole double throw magnetic switch 48 is a first switch, and the relay switch 54 is a second switch.

The process in FIG. 8 may generally begin at block 90 where the pulse generator 12 determines if a magnetic field is detected. In embodiments, the magnetic field can be detected by using a Hall effect, reed switch, magnetoresistive material such as Giant Magneto Resistance (GMR) or BMR, or other suitable sensors. If no magnetic field is detected, the pulse generator 12 operates in the normal mode (block 92). Further, when the pulse generator 12 is operating in normal mode the conductive path between the pulse generator 12 and electrode is established via the first switch (block 94). In embodiments, in the absence of the magnetic field, the magnetic switch 48 connects the pole to the node 50 to create a conductive path between the pulse generator 12 and the electrode 42. When the conductive path between the pulse generator 12 and the electrode 42 via the first switch 48 is established 94, the pulse generator 12 returns to determining if a magnetic field is detected (block 90).

If a magnetic field is detected, the pulse generator 12 operates in the MRI mode (block 96). Further, when the magnetic field is detected, the conductive path provided between the pulse generator 12 and the electrode via the first switch 48 is substantially prevented (block 98). In embodiments, in the presence of the magnetic field, the single-pole of the magnetic switch 48 deflects from node 50 to node 52. Additionally, the second switch 54 monitors a voltage (V) across the second switch (block 100). In certain embodiments, for example, the second switch 54 may monitor a voltage (V) provided by the pulse generator 12. In embodiments, the relay switch 54 monitors the voltage applied across the second switch 54.

After measuring the voltage (V), the second switch 54 determines if the measured voltage (V) is greater than the voltage threshold (Vth) of the second switch 54 (block 102). If V≦Vth, the second switch 54 determines if the second switch 54 is closed (block 104), then the second switch 54 is opened (block 106). In embodiments, the second switch 54 is opened when V≦Vth. If the second switch 54 is already opened 104, the process returns to determining if the magnetic field is still present (block 90).

If V>Vth (block 102), the second switch 54 determines if the second switch 54 is closed (block 108). If the second switch 54 determines that the second switch 54 is open, the second switch 54 is then closed (block 110). In embodiments, the second switch 54 is closed when V>Vth. If the second switch 54 is already closed (block 108), the pulse generator 12 returns to determining if the magnetic field is still present (block 90).

Although several embodiments are disclosed with respect to a cardiac management system 10 deployed in a patient's heart 16 (FIG. 1), the several embodiments are applicable to any system deployed in a patient's body that may be subject to an MRI scan. As an example, the several embodiments are applicable to neuromodulation devices with one or more leads that come into contact with human tissue.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the present disclosure, together with all equivalents thereof.

What is claimed is:

1. A medical device, comprising:
   a pulse generator;
   a lead including an electrode configured to contact body tissue in a body vessel and a lead conductor connecting the pulse generator with the electrode via first and second conductive paths, the first conductive path parallel to the second conductive path;
   a first switch electrically coupled in series between the lead conductor and the electrode, the first switch including a non-conductive state, the non-conductive state preventing formation of the first conductive path between the pulse generator and the electrode in the presence of an MRI magnetic field, the first switch including a conductive state in the absence of the magnetic field, the conductive state allowing formation of the conductive path between the pulse generator and the electrode; and
   a second switch electrically connected in series between the lead conductor and the electrode, the second switch including a non-conductive state preventing formation of the second conductive path between the pulse generator and the electrode, the second switch including a conductive state allowing formation of the second conductive path between the pulse generator and the electrode when a voltage applied across the second switch exceeds a threshold voltage;
   wherein the first switch in the non-conductive state and the second switch in the non-conductive state electrically shields the electrode from at least electromagnetic radiation and induced voltages in the presence of the MRI magnetic field.

2. The medical device of claim 1, wherein
   the first switch is a single-pole double-throw magnetic switch,
   in the absence of the magnetic field, the single-pole double-throw magnetic switch is configured to allow formation of the first conductive path between the pulse generator and the electrode, and
   in the presence of the MRI magnetic field, the single-pole double-throw magnetic switch is configured to connect the pulse generator to the second switch.

3. The medical device of claim 2, wherein the single-pole double-throw magnetic switch is a reed switch.

4. The medical device of claim 1, wherein the first switch comprises magnetoresistive material.

5. The medical device of claim 1, wherein the second switch further comprises a Zener diode bypass.

6. The medical device of claim 1, wherein the second switch is a voltage controlled switch configured to short the lead conductor to the electrode when the voltage applied across the second switch exceeds a predetermined threshold voltage.

7. The medical device of claim 1, wherein the pulse generator is configured to operate in a normal mode in the absence of the magnetic field and in an MRI mode in the presence of the magnetic field.

8. The medical device of claim 7, wherein the voltage applied across the second switch during a therapy pulse when the pulse generator is operating in the MRI mode exceeds the threshold voltage of the second switch.

9. The medical device of claim 1, wherein the second switch receives a signal via a control line from the pulse generator, and wherein the signal directs the second switch to allow formation of the second conductive path between the pulse generator and the electrode during therapy pulses from the pulse generator.

10. The medical device of claim 1, wherein the pulse generator includes a fiber optic line configured to activate the second switch to the conductive state to allow formation of the second conductive path.

11. The medical device of claim 1, wherein
the pulse generator is further configured to emit the one or more therapy pulses at a duration equal to or greater than a threshold duration, and
the second switch is further configured to operate in the closed state upon reception of the one or more therapy pulses having a voltage level exceeding the threshold voltage and a duration exceeding the threshold duration.

12. A method for delivering therapy, comprising:
detecting the presence of a magnetic field at a pulse generator, the pulse generator coupled to a lead including an electrode configured to contact tissue in a body vessel and a lead conductor connecting the pulse generator with the electrode via first and second conductive paths, the first conductive path parallel to the second conductive path;
switching a first switch electrically coupled in series between the pulse generator and the electrode to a conductive state in the absence of the magnetic field, the conductive state of the first switch allowing formation of the first conductive path between the pulse generator and the electrode;
switching the first switch to a non-conductive state in the presence of the magnetic field, the non-conductive state of the first switch preventing formation of the first conductive path between the pulse generator and the electrode;
switching a second switch electrically coupled in series between the pulse generator and the electrode to a non-conductive state when a voltage is applied across the second switch that is less than or equal to a threshold voltage, the non-conductive state of the second switch preventing formation of the second conductive path between the pulse generator and the electrode; and
switching the second switch to a conductive state upon detection of the voltage applied across the second switch exceeding the threshold voltage, the conductive state of the second switch allowing formation of the conductive path between the pulse generator and the electrode,
wherein the first switch in the non-conductive state and the second switch in the non-conductive state electrically shields the electrode from at least electromagnetic radiation and induced voltages in the presence of the MRI magnetic field.

13. The method of claim 12, wherein
the first switch is a single-pole double-throw magnetic switch,
in the absence of the magnetic field, the single-pole double-throw magnetic switch allowing formation of the first conductive path between the pulse generator and the electrode, and
in the presence of the magnetic field, the single-pole double-throw magnetic switch connecting the pulse generator to the second switch.

14. The method of claim 13, wherein the single-pole double-throw magnetic switch is a reed switch.

15. The method of claim 12, wherein the first switch comprises magnetoresistive material.

16. The method of claim 12, wherein the second switch further comprises a Zener diode bypass.

17. The method of claim 12, wherein the second switch is a voltage controlled switch configured to short the lead conductor to the electrode when the detected voltage exceeds the threshold voltage.

18. The method of claim 12, further comprising:
operating the pulse generator in a normal mode in the absence of the magnetic field; and
operating the pulse generator in an MRI mode in the presence of the magnetic field.

19. The method of claim 18, wherein during operation of the pulse generator in the MRI mode, further including:
delivering one or more therapy pulses at a voltage level that exceeds the threshold voltage of the second switch.

20. The method of claim 12, further comprising
receiving a signal at the second switch via a control line from the pulse generator, the signal directing the second switch to allow formation of the second conductive path between the pulse generator and the electrode during a therapy pulse from the pulse generator.

21. The method of claim 12, wherein the pulse generator includes a fiber optic line configured to activate the second switch to the conductive state to allow formation of the second conductive path.

22. The method of claim 12, wherein
receiving the one or more therapy pulses from the pulse generator, the one or more therapy pulses having a duration greater than a threshold duration, and
switching the second switch to the closed state upon reception of the one or more therapy pulses having a voltage level exceeding the threshold voltage and a duration exceeding the threshold duration.

23. A method for delivering therapy, comprising:
operating a pulse generator in a normal mode in the absence of a magnetic field, the pulse generator connected to a lead including an electrode and a lead conductor connecting the pulse generator with the electrode via first and second conductive paths, the electrode configured to contact tissue in a body vessel, the first conductive path parallel to the second conductive path;
operating the pulse generator in an MRI mode in the presence of the magnetic field;
emitting one or more therapy pulses from the pulse generator at a first voltage level when the pulse generator is operating in the normal mode, the one or more therapy pulses at the first voltage level reaching the electrode via the first conductive path; and emitting one or more therapy pulses from the pulse generator at a second voltage level when the pulse generator is operating in the MRI mode, the second voltage level greater than or equal to the first voltage level plus a threshold voltage, the one or more therapy pulses from the pulse generator at the second voltage level reaching the electrode via the second conductive path.

24. The method of claim 23, wherein the one or more therapy pulses from the pulse generator at the second voltage level exceed the threshold voltage of a switch positioned between the pulse generator and the electrode via the second conductive path.

* * * * *